US007416892B2

(12) United States Patent  
Battrell et al.

(10) Patent No.: US 7,416,892 B2
(45) Date of Patent: Aug. 26, 2008

(54) METHOD AND SYSTEM FOR MICROFLUIDIC MANIPULATION, AMPLIFICATION AND ANALYSIS OF FLUIDS, FOR EXAMPLE, BACTERIA ASSAYS AND ANTIGLOBULIN TESTING

(75) Inventors: C. Frederick Battrell, Redmond, WA (US); Mingchao Shen, Lynnwood, WA (US); Bernhard H. Weigl, Seattle, WA (US); Jeffrey M. Houkal, Bellevue, WA (US); Christy A. Lancaster, Seattle, WA (US); Wayne Breidford, Seattle, WA (US)

(73) Assignee: Micronics, Inc., Redmond, WA (US)

( * ) Notice: Subject to any disclaimer, the term of this patent is extended or adjusted under 35 U.S.C. 154(b) by 769 days.

(21) Appl. No.: 10/762,586

(22) Filed: Jan. 21, 2004

(65) Prior Publication Data

US 2005/0013732 A1  Jan. 20, 2005

Related U.S. Application Data

(60) Provisional application No. 60/441,906, filed on Jan. 21, 2003, provisional application No. 60/441,873, filed on Jan. 21, 2003.

(51) Int. Cl.
*G01N 31/00* (2006.01)
*G01N 1/00* (2006.01)

(52) U.S. Cl. .................. 436/17; 436/174; 436/176; 436/177; 435/7.1

(58) Field of Classification Search .................. 436/17, 436/174, 176–177; 435/7.1
See application file for complete search history.

(56) References Cited

U.S. PATENT DOCUMENTS

| 4,326,027 A | 4/1982 | Wenz ............................. 435/7 |
| 4,774,177 A | 9/1988 | Marks ........................... 435/7 |
| 5,004,682 A * | 4/1991 | Roberts et al. ................. 435/6 |
| 5,695,928 A * | 12/1997 | Stewart ......................... 435/5 |

(Continued)

FOREIGN PATENT DOCUMENTS

WO  WO 99/33559 A  7/1999

(Continued)

OTHER PUBLICATIONS

U.S. Appl. No. 10/114,890, filed Apr. 3, 2002, Hayenga et al.

(Continued)

*Primary Examiner*—Brian R. Gordon
(74) *Attorney, Agent, or Firm*—Seed IP Law Group PLLC

(57) ABSTRACT

A microfluidic system for isolation and amplification of DNA or RNA from aqueous solutions and detection of the DNA or RNA on a lateral flow detection strip, including a disposable microfluidic card for use in analysis of bacteria in platelets and an analysis of sexually transmitted diseases (STD) in urine. The card will include an embedded membrane that filters out cells and cellular debris. Any biological debris on the membrane will be lysed and the DNA or RNA amplified via PCR amplification protocol, including appropriate reagents and thermal cycling conditions. The amplified DNA or RNA are transferred to a lateral flow detection strip for a visual diagnostic read out. An alternate embodiment includes a microfluidic card for use in typing antiglobulin assays.

13 Claims, 16 Drawing Sheets

U.S. PATENT DOCUMENTS

| | | | | |
|---|---|---|---|---|
| 5,716,852 | A | 2/1998 | Yager et al. | 436/172 |
| 6,017,721 | A | 1/2000 | Butz | 435/7.25 |
| 6,270,970 | B1 * | 8/2001 | Smith et al. | 435/6 |
| 6,362,003 | B1 * | 3/2002 | Young et al. | 436/10 |
| 6,376,194 | B2 * | 4/2002 | Smith et al. | 435/6 |
| 6,432,212 | B1 | 8/2002 | Hirose et al. | 134/6 |
| 6,503,702 | B1 | 1/2003 | Stewart | 435/5 |
| 6,509,192 | B1 * | 1/2003 | Young | 436/10 |
| 6,524,858 | B1 * | 2/2003 | Zelmanovic et al. | 436/10 |
| 6,581,899 | B2 | 6/2003 | Williams | 251/7 |
| 6,743,399 | B1 | 6/2004 | Weigl et al. | 422/102 |
| 7,151,000 | B2 * | 12/2006 | Prusiner et al. | 436/539 |

FOREIGN PATENT DOCUMENTS

| | | |
|---|---|---|
| WO | WO 99/33559 A1 | 7/1999 |
| WO | WO 02/18823 A | 3/2002 |
| WO | WO 02/18823 A1 | 3/2002 |
| WO | WO 02/22265 A | 3/2002 |
| WO | WO 02/22265 A1 | 3/2002 |

OTHER PUBLICATIONS

Cornish, R. et al., "Factors influencing antibody detection with the DiaMed gel antiglobulin test," *Transfusion Medicine*, 13:243-244, 2003.

Esch et al., "Detection of *Cryptosporidium parvum* Using Oligonucleotide-Tagged Liposomes in a Competitive Assay Format," *Analytical Chemistry*, 73(13):3162-3167, 2001.

Lehmann, R. et al., "Detection of Red Blood Cell Alloantibodies by Gel Centrifugation Test," *Transfusion Medicine and Hemotherapy*, 30:117-122, 2003.

McNeil, P. et al., "Immunology and Clinical Importance of Antiphospholipid Antibodies," *Advances in Immunology*, 49:193-280, 1991.

Novaretti, M.C.Z. et al., "Comparison of conventional tube test with diamed gel microcolumn assay for anti-D titration," *Clin. Lab. Haem.*, 25:311-315, 2003.

Quigley, K. et al., "Application of a direct flow cytometric erythrocyte immunofluorescence assay in dogs with immune-mediated hemolytic anemia and comparison to the direct antiglobulin test," *J Vet Diagn Invest*, 13:297-300, 2001.

Rordorf, C. et al., "A Multidot Immunobinding Assay for Autoimmunity and the Demonstration of Novel Antibodies against Retroviral Antigens in the Sera of MRL Mice," *Journal of Immunological Methods*, 59:105-112, 1983.

Ssebabi, E.C.T., "Enzyme antihuman-globulin test, Technique to detect enzyme autoantibody", *Chemical Abstracts*, 80(23):322, 1974.

Telen, M., "Erythrocyte Blood Group Antigens: Not So Simple After All," *The Journal of The American Society of Hematology*, 85(2):299-306, 1995.

Ylagan et al., "The Antiglobulin Test," *American Association of Blood Banks, Technical Manual*, 11th Edition, pp. 175-187, 1993.

Esch, Mandy B. et al, "Detection of *Cryptosporidium parvum* Using Oligonucleotide-Tagged Liposomes in a Competitive Assay Format," Analytical Chemistry, 73(13):3162-3167, Jul. 1, 2001.

Weigl et al., "Microfluidic Diffusion-Based Separation and Detection", Science 283:346-347, 1999.

* cited by examiner

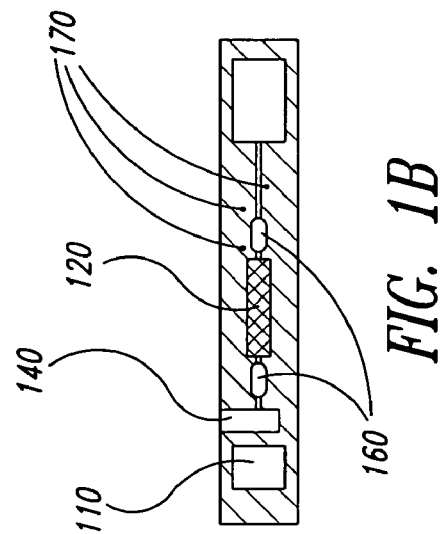
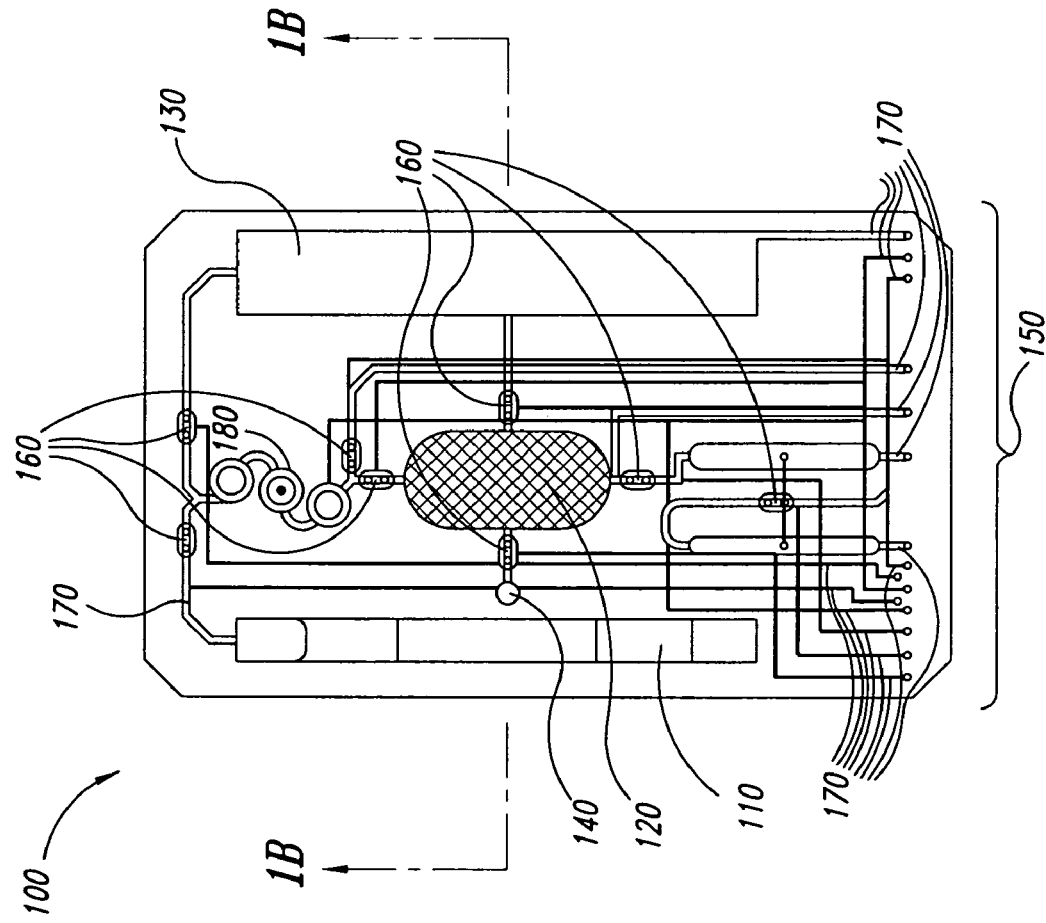

WATER SAMPLE FILTRATION

| Step | Solution | Volume | Pump | Rate | Flow Logic |
|---|---|---|---|---|---|
| 1 | Wash sample | TBD | N/a | TBD | Water sample filtered through the Filter Membrane Module. Target cellular material is on membrane material. |
| 1A | None | N/A | N/A | N/A | The Filter module is removed from filtration apparatus and snapped into the disposable card. |

RUN PROCESS

| Step | Solution | Volume | Pump | Rate | Flow Logic |
|---|---|---|---|---|---|
| 2 | Wash buffer | TBD | 1 | TBD | Pumped across the membrane. Target cellular material remains on the membrane. |
| 3 | Induction solution | 20–40 µl | 2 | TBD | Induction solution that has been pipetted onto the card will be pumped across the membrane. |
| 4 | Wash buffer | TBD | 1 | TBD | Induction solution is washed from membrane with the wash buffer and to waste reservoir. |
| 5 | Series II lysing solution | 20–40 µl | 2 | TBD | A solution to lyse the cells is pumped to the filter cell material and across the membrane. |
| 6 | Wash buffer | TBD | 1 | TBD | Lysing solution is washed from membrane with the wash buffer and to waste reservoir. |
| 7 | NASBA w/o enzymes | 4–40 µl | 3 | TBD | NASBA solution is pumped to the filter and lysed cell material. |
| 8 | Wash buffer | TBD | 1 | TBD | The NASBA solution is washed from membrane with the wash buffer and to waste reservoir. |
| 9 | NASBA enzyme solution | 4–8 µl | 3 | TBD | NASBA solution with enzyme is pumped to the cellular material on the membrane. |
| 10 | Wash buffer | TBD | 1 | TBD | The NASBA solution is washed from the membrane and to waste reservoir. |
| 11 | Detection probe solution | 2.5 – 5.0 µl | 4 | TBD | Detection solution is pumped to the material on the membrane. |
| 12 | Thermo-cycling step | N/a | N/a | | The card is removed from instrument. The card with cellular material is thermo-cycled to amplify the DNA signal. |
| 13 | Wash buffer | TBD | 1 | TBD | Detection probe solution is washed from the membrane where it is exposed to the lateral flow detection strip. |

DETECTION PROCESS

| Step | Solution | Volume | Pump | Rate | Flow Logic |
|---|---|---|---|---|---|
| 14 | Wash buffer | TBD | 1 | TBD | Channel opened to lateral flow detection strip and Buffer pumped to the amplified DNA on the membrane to the lateral flow detection strip. |

*FIG. 4C*

METHOD AND SYSTEM FOR MICROFLUIDIC MANIPULATION, AMPLIFICATION AND ANALYSIS OF FLUIDS, FOR EXAMPLE, BACTERIA ASSAYS AND ANTIGLOBULIN TESTING

CROSS-REFERENCE TO RELATED APPLICATIONS

This application claims the benefit of U.S. Provisional Patent Application No. 60/441,906, filed Jan. 21, 2003, and 60/441,873, filed Jan. 21, 2003, both of which are hereby incorporated by reference in their entirety.

BACKGROUND OF THE INVENTION

1. Field of the Invention

The present invention relates generally to microfluidic devices and analysis methods, and more particularly, to microfluidic devices and methods for the manipulation, amplification and analysis of fluid samples including, for example, blood platelet bacteria assays and antiglobulin testing.

2. Description of the Related Art

Microfluidic devices have become popular in recent years for performing analytical testing. Using tools developed by the semiconductor industry to miniaturize electronics, it has become possible to fabricate intricate fluid systems that can be inexpensively mass-produced. Systems have been developed to perform a variety of analytical techniques for the acquisition and processing of information.

The ability to perform analyses microfluidically provides substantial advantages of throughput, reagent consumption, and automatability. Another advantage of microfluidic systems is the ability to integrate a plurality of different operations in a single "lap-on-a-chip" device for performing processing of reactants for analysis and/or synthesis.

Microfluidic devices may be constructed in a multi-layer laminated structure wherein each layer has channels and structures fabricated from a laminate material to form microscale voids or channels where fluids flow. A microscale or microfluidic channel is generally defined as a fluid passage which has at least one internal cross-sectional dimension that is less than 500 µm and typically between about 0.1 µm and about 500 µm.

U.S. Pat. No. 5,716,852, which patent is hereby incorporated by reference in its entirety, is an example of a microfluidic device. The '852 patent teaches a microfluidic system for detecting the presence of analyte particles in a sample stream using a laminar flow channel having at least two input channels which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known as a T-Sensor, allows the movement of different fluidic layers next to each other within a channel without mixing other than by diffusion. A sample stream, such as whole blood, a receptor stream, such as an indicator solution, and a reference stream, which may be a known analyte standard, are introduced into a common microfluidic channel within the T-Sensor, and the streams flow next to each other until they exit the channel. Smaller particles, such as ions or small proteins, diffuse rapidly across the fluid boundaries, whereas larger molecules diffuse more slowly. Large particles, such as blood cells, show no significant diffusion within the time the two flow streams are in contact.

Typically, microfluidic systems require some type of external fluidic driver to function, such as piezoelectric pumps, micro-syringe pumps, electroosmotic pumps, and the like. However, in U.S. patent application Ser. No. 09/684,094, which application is assigned to the assignee of the present invention and is hereby incorporated by reference in its entirety, microfluidic systems are described which are completely driven by inherently available internal forces such as gravity, hydrostatic pressure, capillary force, absorption by porous material or chemically induced pressures or vacuums.

In addition, many different types of valves for use in controlling fluids in microscale devices have been developed. For example, U.S. Pat. No. 6,432,212 describes one-way valves for use in laminated microfluidic structures, U.S. Pat. No. 6,581,899 describes ball bearing valves for use in laminated microfluidic structures, and U.S. patent application Ser. No. 10/114,890, which application is assigned to the assignee of the present invention, describes a pneumatic valve interface, also known as a zero dead volume valve, for use in laminated microfluidic structures. The foregoing patents and patent applications are hereby incorporated by reference in their entirety.

Although there have been many advances in the field, there remains a need for new and improved microfluidic devices for manipulating, amplifying and analyzing fluid samples.

One example of an area needing new and improved microfluidic devices is with respect to bacterial and antiglobulin analysis. Bacterial sepsis caused by bacterially contaminated platelets is the cause of blood transfusion transmitted infections up to 250 times more often than HIV, hepatitis C or West Nile virus. Of the 4 million platelet units transfused each year in the United States, 1,000 to 4,000 are contaminated with bacteria, and 167 to 1,000 cases of clinical sepsis result. Twenty to 40 percent of patients with clinical symptoms die.

Current Platelet Bacteria Assays

Platelet screening is not routinely performed in the US prior to transfusion; however, AABB has proposed a new standard requiring pre-transfusion testing of platelets for bacterial contamination.

Several methods are currently being used outside the US:

Standard cell culture: platelets are cultured in Petri-dish, and bacteria are detected after staining. This method is very time consuming, is not automated, and requires a significant amount of platelets.

Pall Bacteria Detection System (Pall BDS): uses changes in oxygen concentration as a result of bacterial growth. Since bacteria consume oxygen, abnormally low levels of oxygen in a platelet sample indicate the presence of bacteria.

BioMéneux's BacT/Alert system detects the presence of bacteria by tracking their production of carbon dioxide.

Hemosystem is developing a system for bacterial detection in platelets concentrates based on fluorescence detection after bacteria labeling with a fluorescent marker.

BRIEF SUMMARY OF THE INVENTION

Aspects of the current invention include a platelet-specific bacteria assay system for urine and whole blood analysis. This system, known as the BAC Card system, is based on the identification of bacterial DNA detection through bacteria lysing and subsequent isothermal DNA amplification and detection. Yet another embodiment of the present invention provides analysis and detection of urine to determine the presence of sexually transmitted diseases.

The following exemplary steps are performed on the microfluidic card according to aspects of the present invention: collect a sample from the blood platelet bag is placed on an inlet of the lab card; lyse bacteria (as well as remaining white cells) in a lysing channel; capture bacterial DNA onto a solid substrate in the amplification chamber; pump DNA primers, designed from genes encoding the small subunit of the RNA molecule of the ribosome (16S rRNA or SSU rRNA genes) over the solid substrate followed by wash buffers, as the amplification chamber is exposed to an isothermal amplification temperature profile; pump amplified 16S rRNA DNA over a lateral flow strip; visual indication of the presence of bacterial DNA.

Further aspects of the invention include a microfluidic system for typing antiglobulin assays including a substrate having flow channels therein, an inlet port for receiving a blood sample, a filter for separating red cells and plasma, a system for mixing a portion of the plasma with appropriate reagents, a heating source, a port for adding antiglobulin serum, and a window for visually reviewing the test results.

BRIEF DESCRIPTION OF THE SEVERAL VIEWS OF THE DRAWINGS

FIG. 1A illustrates a schematic of a microfluidic analysis card in accordance with principles of the present invention.

FIG. 1B is a cross section of FIG. 1A along line 1B-1B.

FIG. 4C is a chart illustrating the steps of the flowchart contained in FIG. 4B.

DETAILED DESCRIPTION OF THE INVENTION

Figure 2:
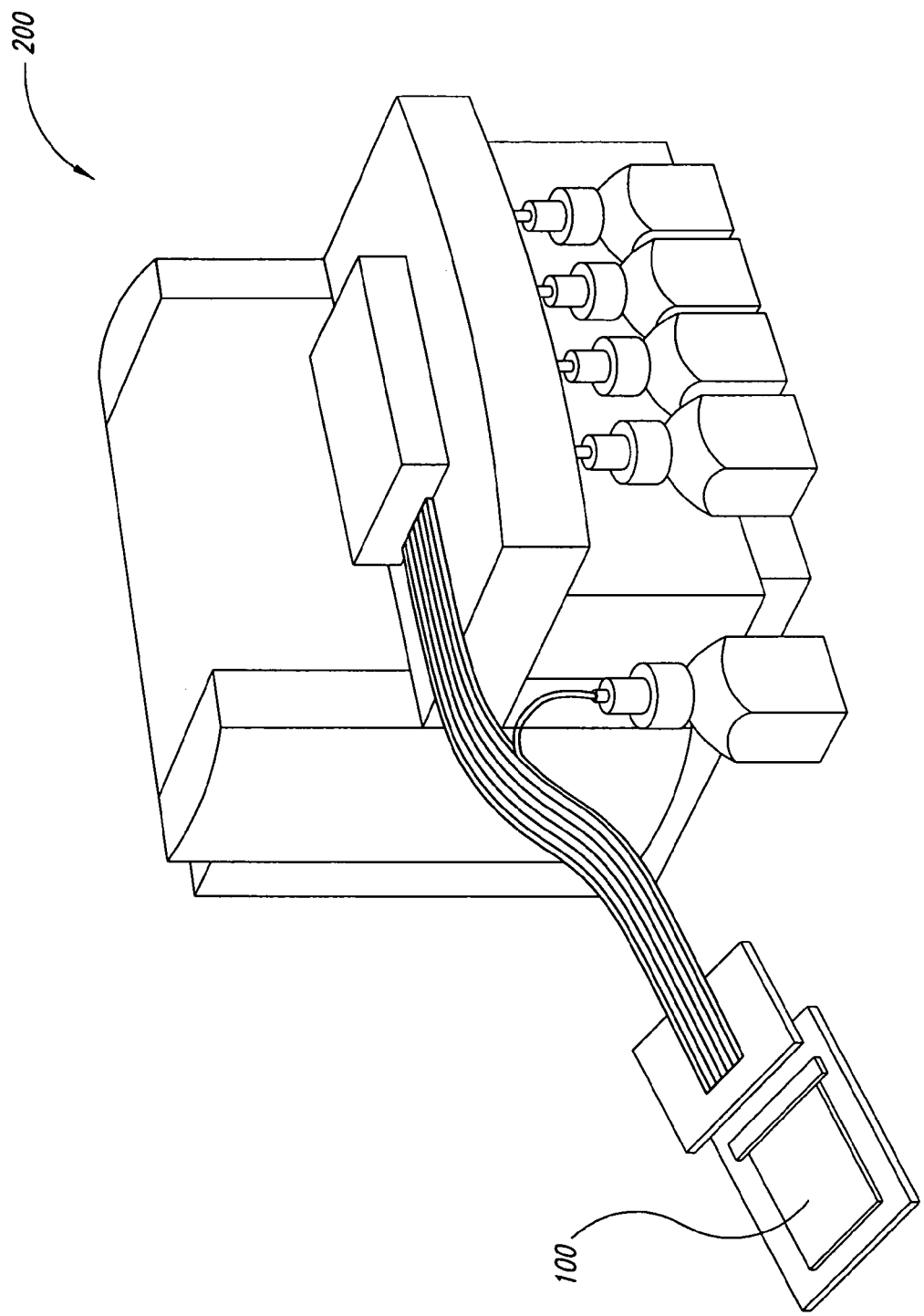
FIG. 2 illustrates a schematic of an instrument for actuating fluid flow in the microfluidic analysis card according to principles of the present invention.

As noted previously, the present invention relates to microfluidic devices and methods utilizing a plurality of microfluidic channels, inlets, valves, membranes, pumps, liquid barriers and other elements arranged in various configurations to manipulate the flow of a fluid sample in order to prepare such sample for analysis and to analyze the fluid sample. In the following description, certain specific embodiments of the present devices and methods are set forth, however, persons skilled in the art will understand that the various embodiments and elements described below may be combined or modified without deviating from the spirit and scope of the invention.

As illustrated in FIGS. 1A and 1B, one embodiment of the present invention includes a disposable lab card 100 device that is a bacterial assay system for urine and whole blood analysis. The system includes fluid miniaturization capabilities in order to perform lysing and DNA capture. On-card isothermal amplification is then performed in order to detect and identify bacteria in a sample.

Further aspects of the present invention include a microfluidic system for isolation and amplification of DNA from aqueous solutions and detection of the DNA on a strip reader, including a disposable card for use, for example, in analysis of *E. coli* in water as well as analysis of sexually transmitted diseases (STD). According to one aspect of the invention, the card may include an embedded membrane that permits quantities of fluid, for example, approximately 100 ml of water or 10 milliliters of urine, to pass through the membrane. As fluid passes through the membrane, the membrane filters out cells and cellular debris. Any biological debris on the membrane may be lysed and the DNA amplified via PCR amplification protocol (appropriate reagents and thermal cycling conditions). The amplified DNA may then be transferred to a lateral flow detection strip for the diagnostic read out.

Further aspects of the invention include a microfluidic system for typing antiglobulin assays. The Antiglobulin card (the AHG card) addresses the issue that many red cell antibodies are IgG and do not directly agglutinate sensitized red blood cells. Once these antibodies or the complement activated by these antibodies are attached to sensitized red blood cells, they are detected by the addition of an anti-human globulin or an anti-complement reagent. This embodiment includes three areas: a microfluidic separator; a room-temperature microfluidic circuit, and a 37 degree Celsius microfluidic circuit.

Bacterial Assay Microfluidic Card

Aspects of the current invention include a platelet-specific bacteria assay system for urine and whole blood analysis. This system, known as the BAC Card system, is based on the identification of bacterial DNA detection through bacteria lysing and subsequent isothermal DNA amplification and detection.

All steps are performed on the microfluidic card. As compared to prior art methods, the whole process of the current invention will take a reduced amount of time, for example, less than 90 minutes; and will have an increased sensitivity, for example, a sensitivity of approximately 100 bacteria/mL. The following include exemplary steps in the process:

A sample is collected from the blood platelet bag is placed on an inlet of the lab card Bacteria (as well as remaining white cells) are lysed in a lysing channel Bacterial DNA is captured onto a solid substrate in the amplification chamber DNA primers, designed from genes encoding the small subunit of the RNA molecule of the ribosome (16S rRNA or SSU rRNA genes) are pumped through over the solid substrate followed by wash buffers, as the amplification chamber is exposed to an isothermal amplification temperature profile Amplified 16S rRNA DNA is then pumped over a lateral flow strip, where the presence of bacterial DNA is visually indicated FIG. 2 illustrates the bacterial assay card (BAC) interfacing with an instrumentation system 200 that may be used to operate the BAC Card 100.

Antiglobulin (AHG) Card

Yet another embodiment of the present invention is an assay card for Antiglobulin testing, (the AHG Card).

The AGH Card addresses the issue that many red cell antibodies are IgG and do not directly agglutinate the sensitized red blood cells. Once these antibodies or the complement activated by these antibodies are attached to sensitized red blood cells, they are detected by addition of an anti-human globulin and or anti-complement reagent.

Figure 3:
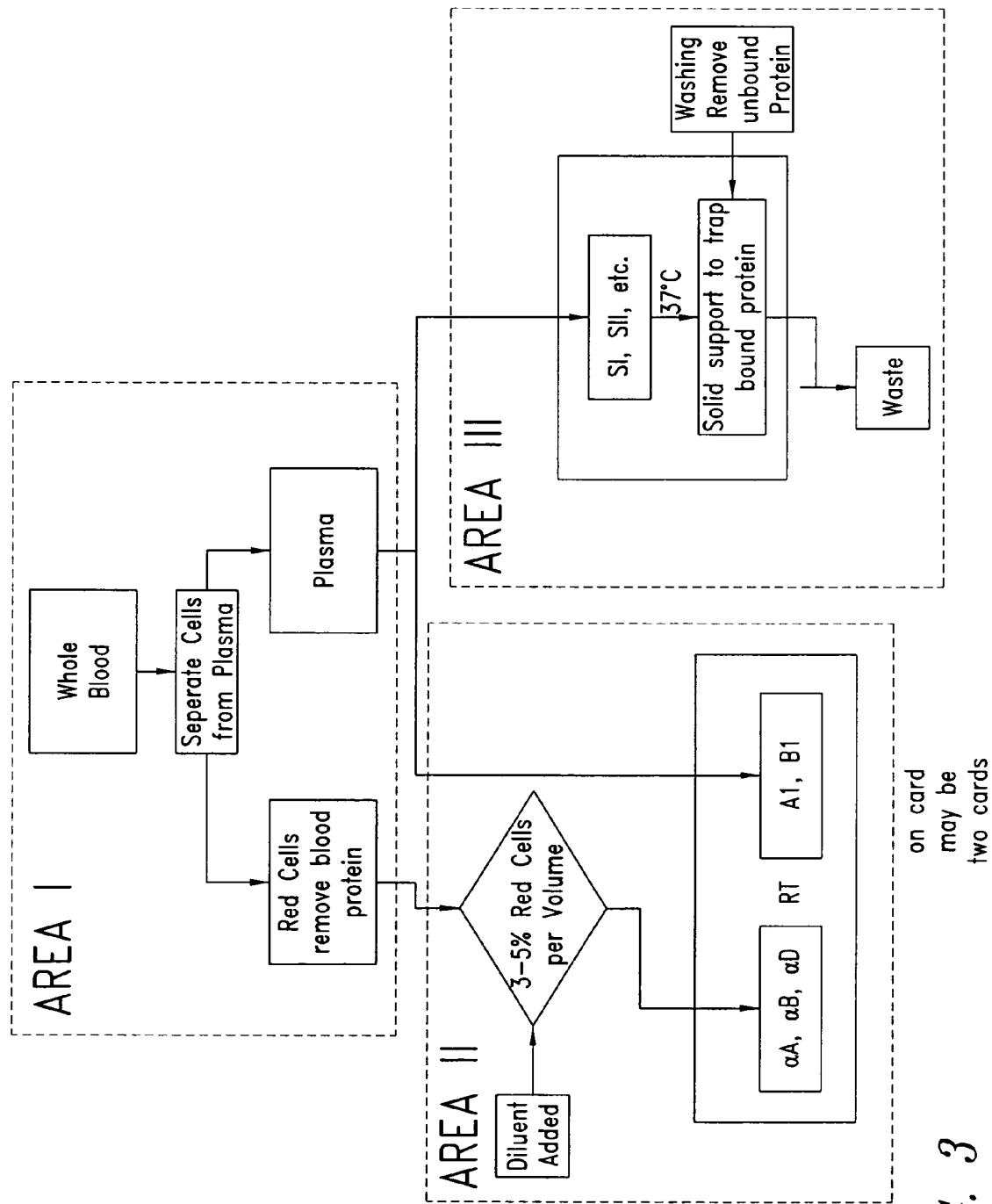
FIG. 3 illustrates a process flowchart for a diagnostic device-performing microfluidic antiglobulin analysis in accordance with principles of the present invention.

As illustrated in FIG. 3, according to one embodiment of the present invention, a microfluidics based card will perform all functions required for the ABO/Rh and AHG assay on board the card. This embodiment includes three areas:

I. a microfluidic plasma separator
II. a room-temperature microfluidic circuit, and
III. a 37° C. microfluidic circuit Areas II and III are incubated at different temperatures using a custom heat pad incubator. The AHG Card does not require any external pumping or detection means. Fluids are moved through the card using integrated on-card bellows pumps as described in applicants co-pending application filed Jan. 14, 2004 entitled MICROFLUIDIC DEVICES FOR FLUID MANIPULATION AND ANALYSIS, serial number not yet assigned, herein incorporated in its entirety by reference. Results are visually interpreted.

In Accordance With One Aspect of the Present Invention and According to the Flow Chart Shown in FIG. 3, the Following Steps may be Performed on the Card:

1. In Area I, a whole blood sample is microfluidically separated into red cells (Sample 1) and plasma (Sample 2) without centrifugation.
2. Sample 2 is separated into two aliquots—Sample 2a and Sample 2b. Sample 2a is moved to Area II, and Sample 2b is moved to Area III.
3. In Area II, residual plasma proteins are removed from the red-cell rich aliquot by diffusion-based separation, and the aliquot is diluted in saline to a 3-5% of red cells concentration. Then, in three individual microchannels, Sample 1 is reacted with Anti-A, Anti-B, and Anti-D reagents, and the reactions are visually interpreted in the reaction windows. Concurrently, Sample 2a is reacted in two individual microchannels with $A_1$ and B red blood cells, and the reactions are also visually interpreted.
4. In Area II, the card is brought to 37° C.; reagents, red cells, SI and SII (diluted red cells) are incubated for 15-60 minutes with the plasma. If the serum contains an antibody specific for an antigen on the red cells, the antibody will sensitize the cells (but not agglutinate them, if the antibody is IgG). The mixture flows through a separation medium where proteins are removed from the Sample. After a washing step, AHG serum is added in a microchannel, and the test results are visually interpreted.

With respect to the above-mentioned steps, step 1 discusses microfluidically separating the blood sample into red cells and plasma without centrifugation. This may be accomplished in a number of different ways. In one embodiment, a diffusion-based separation is used as discussed in U.S. Pat. No. 5,932,100 herein incorporated by reference. The differential transport requires an extraction fluid that has been omitted from the above referenced flow diagram.

In yet another embodiment, particle lift effect may be used. Particles flowing in the microchannel flow away from the wall leaving a layer immediately adjacent to the channel that is particle-free. This thin particle-free layer may be stripped from the fluid flow by several means including perforating the wall of the channel, providing vents, or similar means. The particles continue to migrate toward the center despite stripping off various particle-free fluid, and so the process may be repeated by providing a flow channel in the loop.

In an alternative embodiment, a filter may be used filtering the particle-free fluid. Typically, when a filter is used it literally clogs with red cells, however, according to the present invention only a small amount of plasma is needed to perform the operation and therefore a filter is adequate.

In yet another alternative embodiment, a means of separate the red cells and plasma includes using a tangential flow filter. In yet another embodiment of the separation means, sedimentation may be used to allow the blood sample to settle, thus allowing the red cells to slowly settle while taking a thin layer off of the top. Again, due to the small quantity of plasma required, sedimentation is a viable alternative.

In yet another embodiment of the present invention, step 3 and step 2 may be combined such that diffusion-based separation is used to completely remove the plasma and plasma proteins from the red cell aliquot.

Step 3 calls for the reactions of the antibodies A, B, and D reagents with the blood sample. These combined flows may be mixed through diffusion, sedimentation, and coagulation as disclosed in U.S. Pat. No. 6,136,272 herein incorporated in its entirety by reference.

As further illustrated in the flowchart on FIG. 4, and in combination with the disclosure contained above regarding the blood typing microfluidic system, the steps outlined with respect to the anti-globulin assay may be performed on a single card or alternatively, may be performed on two or more cards. It may be advantageous, for example, to remove the functions performed in area 3 in order to provide incubation while maintaining room temperature for the functions in area 2. However, in an alternative embodiment, it is possible to perform all of the functions outlined in areas 1, 2, and 3 and to provide an on-card heating element such as resistor that specifically heats and incubates the plasma mixture.

In this embodiment of a microfluidic diagnostic system, due to the fragile nature of the red cells and diluted red cells known as SI and SII, these reagents cannot be preloaded onto the card as, for example, the antibody-A, B, and D reagents can be.

The heating means used to bring the portion of the card containing the plasma mixture to 37° C. may be any known heating means include a flat metal resistor, infrared heating, radiant heating, a Peltier heater, liquid heating, or other appropriate means.

Bacteria Assay General Description

According to one embodiment of the current invention, the Single Analyte Diagnostic Device/System (SADD/S) permits the isolation and amplification of DNA from aqueous sample solutions. The amplified DNA will be transferred from the filter membrane to a lateral flow detection strip that will be used for a diagnostic reading.

In one exemplary use, the device/system will be used for the isolation and amplification of DNA found in a water sample for the detection of bacteria including, for example, *Escherichia. coli., Staphylococcus aureus, Pseudomonas aeruginosa, Salmonella* spp., *Staphylococcus epidermidis, Klebsiella pneumoniae, Enterobacter cloacae,* β-*Streptococcus, Serratia marcescens,* and/or *Bacillus cereus.*

The isolation and fluidic preparation for thermal amplification will take place on the disposable card while in place on the instrument. The card will be removed from the instrument for the incubation required to complete the DNA amplification. After incubation, the card will be returned to the instrument where the amplified DNA will be transferred to the detection strip for a diagnostic reading.

Another use for the present invention is the isolation and amplification of DNA from urine for the detection of sexually transmitted diseases.

Figure 4A:
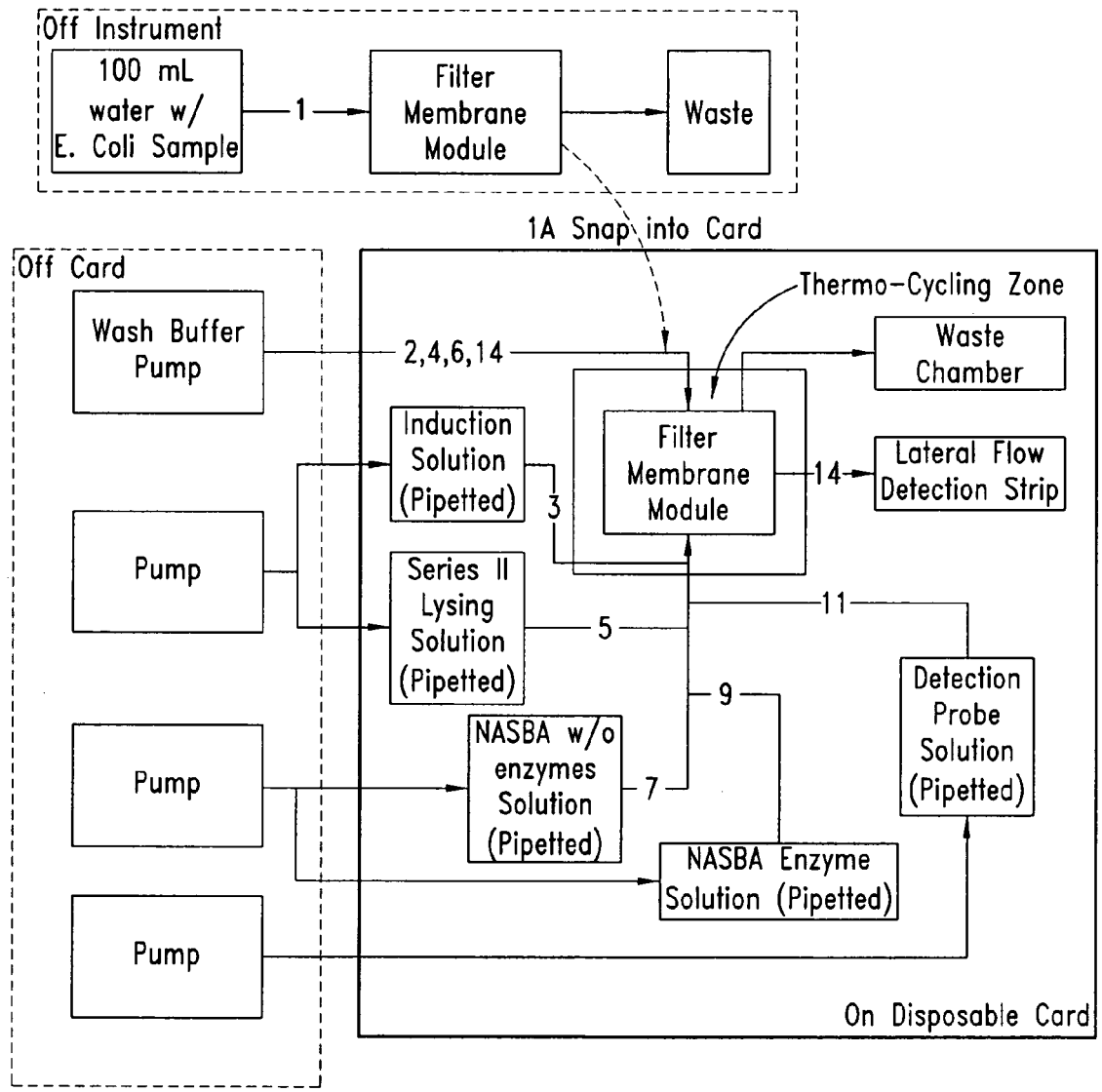
FIG. 4A illustrates a process flowchart for bacteria diagnostic devices for detecting bacteria in platelets in accordance with principles of the present invention.
Figure 4B:
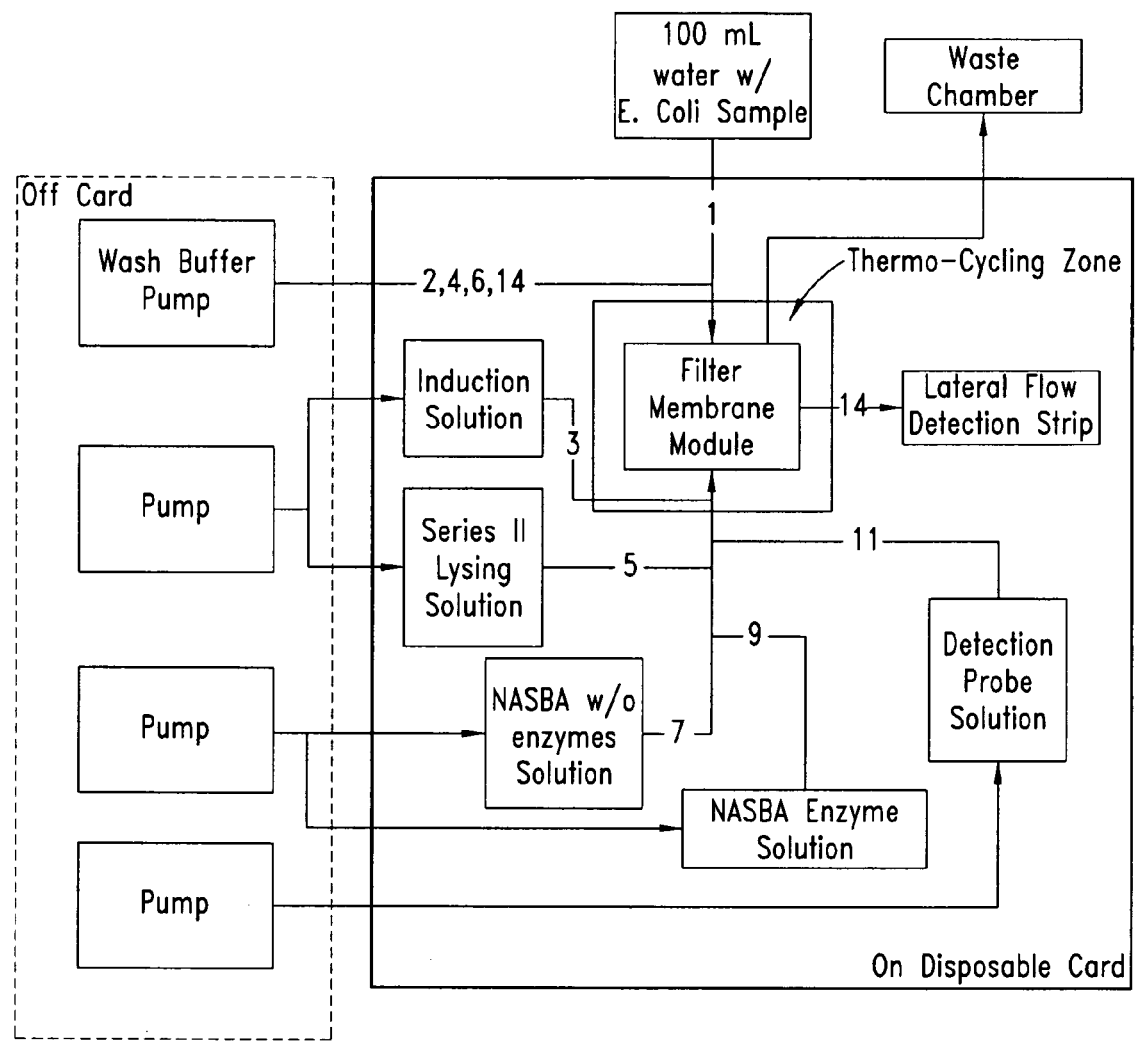
FIG. 4B is yet another embodiment of the present invention illustrating a flowchart for processing a bacteria diagnostic device for protecting bacteria in platelets in accordance with principles of the present invention.

FIGS. 4A and 4B illustrate a schematic flowcharts illustrating embodiments of the BAC card. FIG. 4C provides a written description of each step shown in the flowcharts of FIGS. 4A and 4B. FIG. 4A illustrates an embodiment having a Filter Membrane Module (FMM) that can be snapped into the card after capturing the sample for analysis. FIG. 4B illustrates an embodiment having an FMM that is mounted in the microfluidic card.

The SADD system includes three major components:

A diagnostic disposable microfluidic card which contains filter membrane that has target cells that have been filtered from water samples, and a lateral flow detection strip which will be used to detect the presence of *E. coli* or other bacteria in the water samples tested;

An instrument supporting and controlling the fluidics on the disposable card; and The software that will allow instrument control to drive the fluidics for amplification and detection.

The microfluidic card, instrument and software will be described in further detail below.

Description of Disposable Microfluidic Card

Figure 5:
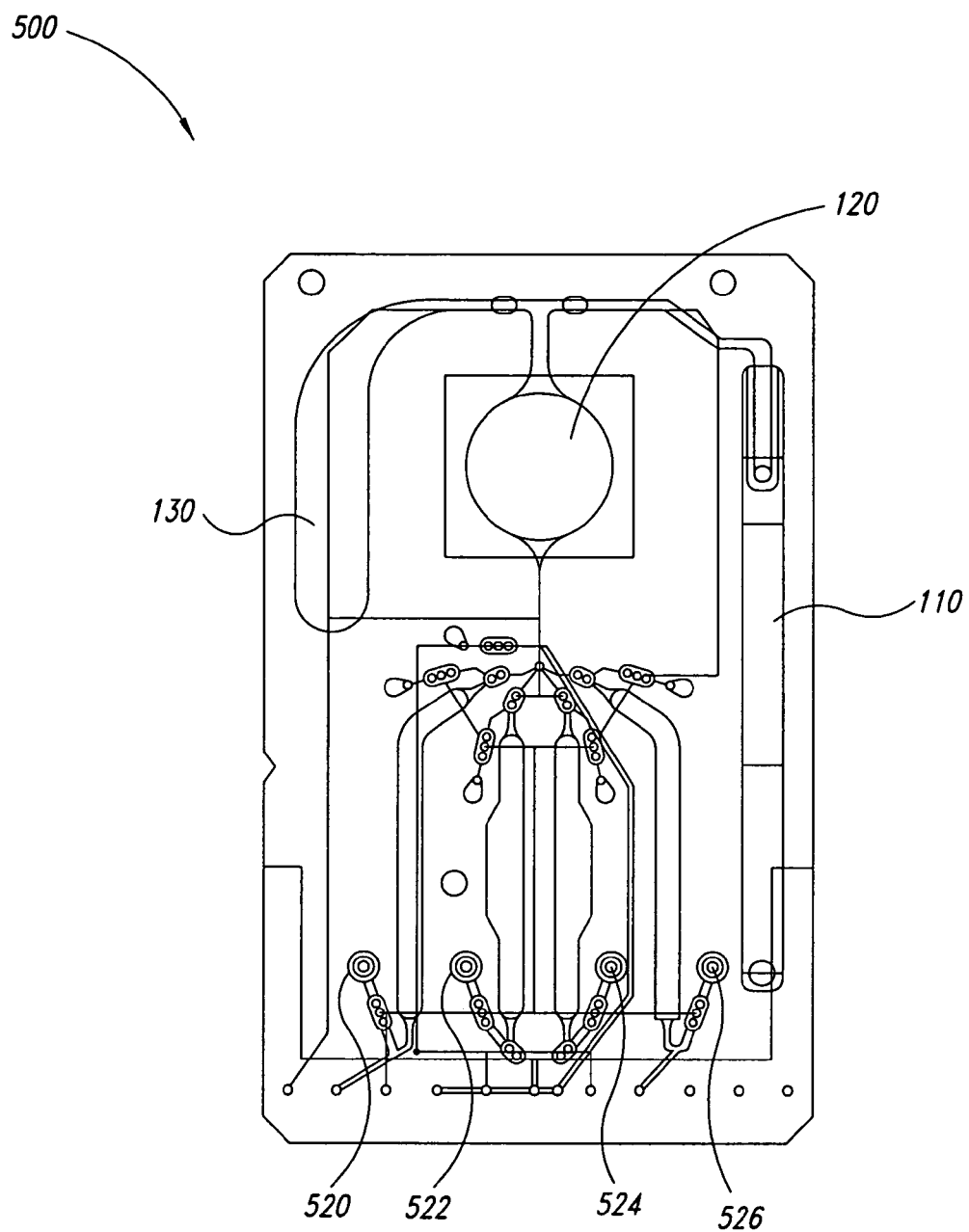
FIG. 5 is a schematic of the microfluidic device in accordance of the flowchart of FIG. 4.

The SADD/S disposable microfluidic card is a multi-layer microfluidic card. FIGS. 1A, 1B and 5 illustrate embodiments of the microfluidic card. FIG. 1A illustrates a microfluidic card 100 having a membrane or filter 120 contained on the card. Also contained on the card is a waste chamber or reservoir 130, a lateral flow detection strip 110, and microfluidic valves 170 and microfluidic flow channels 170. The microfluidic card 100 further may contain a port 140 for pipetting or otherwise dispensing sample to the card. The microfluidic card 100 further contains microfluidic pump interface ports 150 in accordance with one embodiment of the present invention. These interface ports 150 interface with the instrument system described in further detail herein. In accordance with one aspect of the current invention, the microfluidic card may further contain an amplification chamber 180.

FIG. 1B is a cross section along line 1B-1B of the microfluidic card of FIG. 1A. FIG. 1B illustrates exemplary locations within the thickness of the card of various components of the card. Microfluidic flow channels 170 are positioned at various heights in the card so to interface with valves, reservoirs and ports. Optional input port 140 extends to and opens to an exterior of the card surface. Reservoirs, lateral flow strips, flow channels, valves and the like are contained within the microfluidic card.

FIG. 5 is another embodiment illustrating a microfluidic card 100 having a membrane or filter 120 contained on the card. Also contained on the card is a waste chamber or reservoir 130, a lateral flow detection strip 110, microfluidic reservoirs 520, 522, 524, 526, microfluidic flow channels 170, and an amplification chamber or reservoir. The microfluidic reservoirs 520, 522, 524, 526, may for example contain series II lysing, NASBA without enzymes, NASBA with enzymes, an induction solution, detection solution, wash solution, or other appropriate materials.

Figure 6:
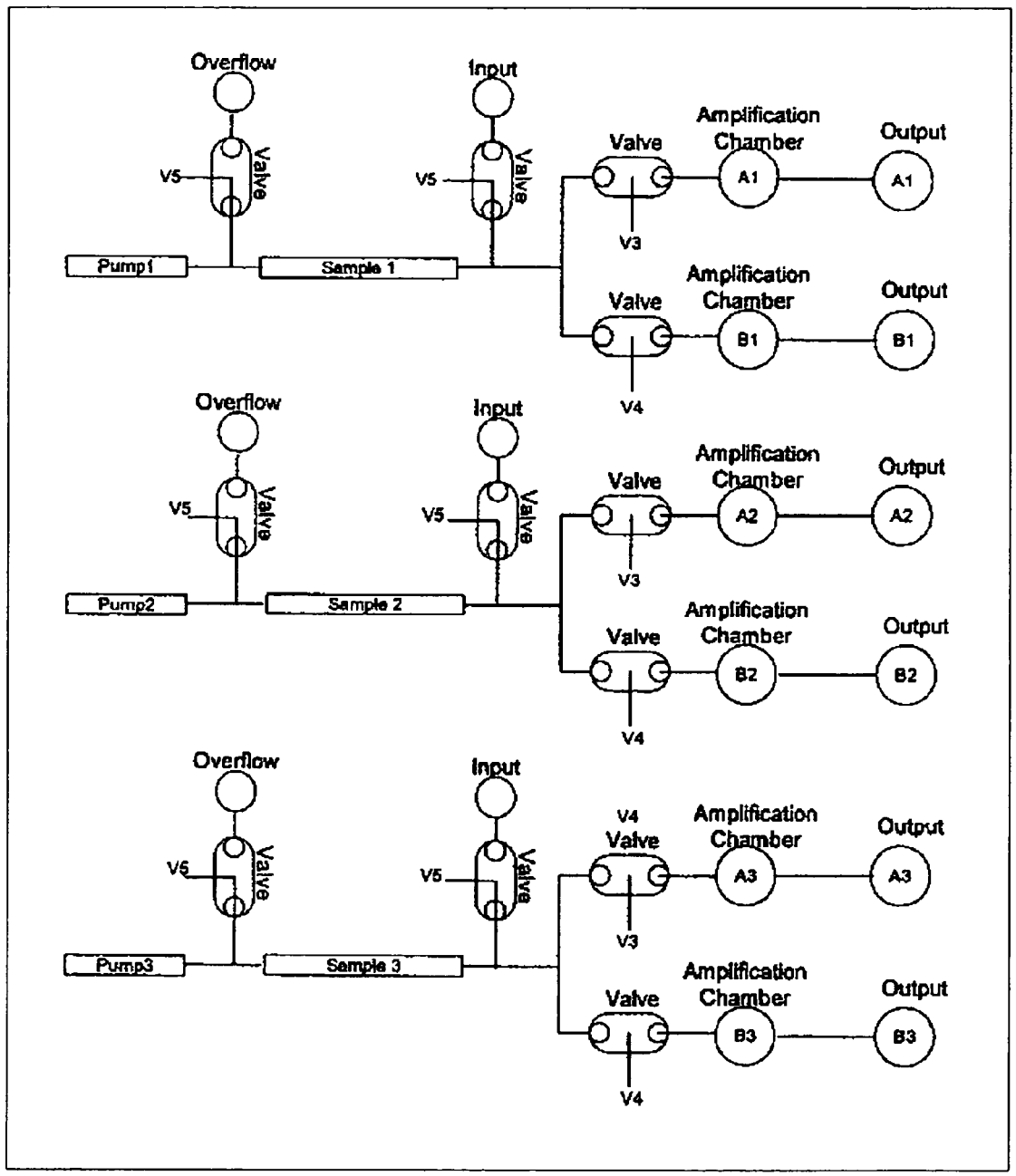
FIG. 6 is flowchart of an exemplary bacteria assay card in accordance with principles of the present invention.

FIG. 6 shows an illustrative schematic example of a microfluidic card containing multiple independent systems for collection, lysing, washing, amplification and detection of a fluid sample in accordance with principles of the present invention.

Figure 7:
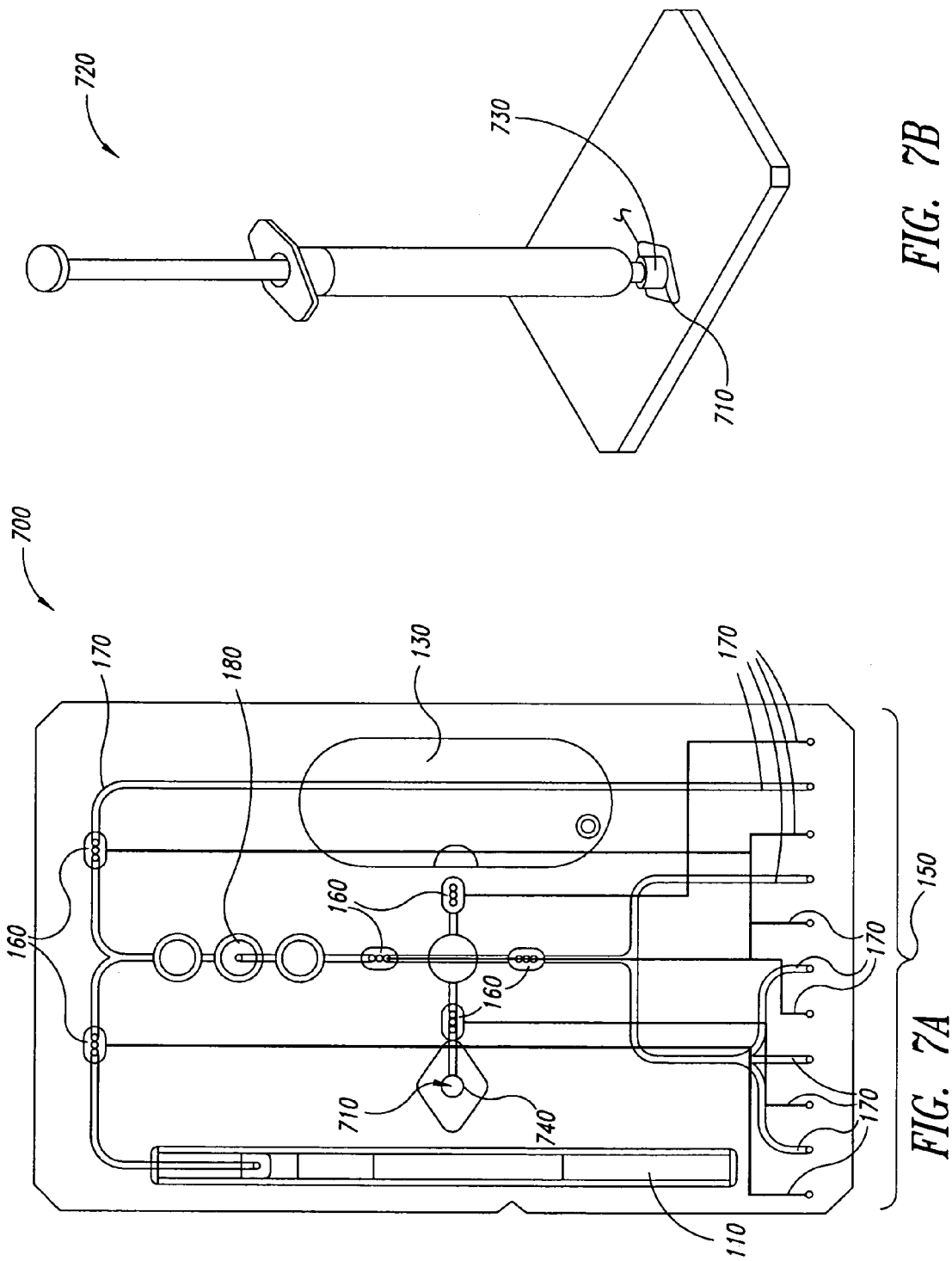
FIGS. 7A and 7B are illustrations of one embodiment of the bacteria assay card illustrating the connection port for a syringe in accordance with principles of the present invention.

FIGS. 7A and 7B illustrate yet another example of a microfluidic card 700 according to principles of the present invention further including an inlet port 710 in the microfluidic card 700. A syringe 720 is shown in FIG. 7B for introducing the liquid sample to the microfluidic card. Alternatively, a pipette or other appropriate device may be used. In one embodiment, the outlet 730 for the syringe 720 is configured to mate with the inlet port 740 of the microfluidic card 700.

The BAC card may consist of the following components in accordance with one embodiment of the present invention:

Laminate Layers: The layers are micro-machined laminates to facilitate coordinated flow through the cards as prescribed. The assembled laminates will form a card that is approximately 3.25 inches×2.5 inches in size. The card thickness will vary depending on the number of layers.

Lateral Flow Strip: The lateral flow strip will be embedded into the card laminate structure to facilitate the detection of isolated and amplified DNA of the target cells. One exemplary detection strip is 1.25 mm thick (0.050 inch) and approximately 2.5-3.0 mm wide by 25 mm in length.

Solution Reservoirs: Five solution reservoirs are on card to allow the user to pipette onto the card the solutions for isolation, detection and amplification of target DNA. In the exemplary embodiment, three reservoirs will allow loading a minimum 40 μL of solution. Two reservoirs will allow the loading of approximately 10 μL of solution.

Waste Reservoir: The waste reservoir will allow the collection and containment of fluids used during the isolation and amplification step of the process. In the exemplary embodiment, the waste reservoir will collect approximately 750 μL of waste solution.

Filter Membrane Module: The filter membrane module is a component that contains the filter membrane used to collect (bind) the target cells of the sample. In the exemplary embodiment, the module will allow filtration of the 100 mL water sample prior to the amplification and incubation process conducted on the card. In this embodiment, the filter material is a 0.17 mm (0.007 in) thick nylon membrane of 13 mm diameter. After filtering the water sample, the Filter Membrane Module (FMM) will be removed from the filtering apparatus and inserted into the disposable card for further processing.

Performance/Compatibility Requirements of the Microfluidic Card

In the exemplary embodiment, one design goal of the microfluidic card is that microfluidic function of the card over a series of sample assays as outlined in this specification will have 95% confidence of greater than 80% reliability.

Operation of the card shall be such that during the Initialization and Detection Process, all fluid will remain contained on the card. No leaking of the card shall be allowed.

The materials used in the design and fabrication of the disposable card shall:

Allow aqueous fluids to fill channels without formation of bubbles and voids that significantly affect successful function of the lab card.

Be compatible with the solutions and materials used for the filtration, amplification and determination of the target sample. The laminates shall not be dissolved or abraded by the solutions, and shall not cause the fluids to become optically turbid after exposure.

Be compatible with the incubation temperatures and exposure times outlined in the thermo-cycling regiment of this specification.

Not leach components that will interfere with the filtration, amplification and diagnostic detection of target material.

The disposable card shall be optically transparent in the area used for reading the visual detection of the target material.

The disposable card shall be able to be used under normal laboratory conditions (10-30° C. and 5%-90% relative humidity) except for thermal cycling processes, and be operable up to 10,000 feet above sea level.

The microfluidic card will be provided clean but not sterile. Cards will be free of particulates and other contamination that will interfere with filtration, amplification and detection.

Reagent Reservoirs: There are two reservoirs on the instrument of this embodiment. One reservoir contains the needed wash buffer. The second reservoir contains the flourinert buffer.

Reagent Supply Lines: The reagent supply lines are connected to reagent storage reservoirs that are used during the operation of the instrument.

Vacuum/Pressure Valve Controller: Valves on the cards in the described embodiment are operated pneumatically. The vacuum/pressure valve controller unit comprised of an array of computer-controlled electronic valves that allow the on-chip valves to be exposed to either vacuum or pressure supplied by a unit housing a vacuum pump and an air pressure pump.

Serial Port: A serial port will be used for the initial feasibility instrument. The port is used for communication between the instrument platform and a microprocessor.

| Product Specifications According to One Embodiment of the Present Invention | | | | | |
|---|---|---|---|---|---|
| | Solutaion | Amount | Dimensions | On card | Off card |
| Sample | Water | 100 mL | | | X |
| Induction Solution | | 20-40 µL | | X | |
| Series II Solution | | 20-40 µL | | X | |
| NASBA Master Mix w/o enzymes Solution | | 4-40 µL | | X | |
| NASBA enzyme Solution | | 4-8 µL | | X | |
| Detection Probe Solution | | 2.5 µL | | X | |
| Wash buffer | TRIS Buffer Tris Hydroxymethylaminoethane | 3 × 50 µL | | | X |
| Membrane | | | 13 mm diameter circle × 0.17 mm | X | |
| Lateral Flow Strip | | | 2.5-3 mm × 25 mm × 1.25 mm | X | |
| Waste | | >100 mL | | | X |

Description of the Instrument System

The instrument supporting and controlling the fluidics on the microfluidic card as shown in FIG. 2 may be small enough to be portable. The instrument includes a manifold that interfaces with the microfluidic card. The SADD/S instrument will be is a computer-controlled platform. According to one embodiment of the present invention, the instrument will include the following components:

Manifold Assembly: The manifold secures the disposable card used during the diagnostic test. The manifold has select number of solenoid-operated pneumatic valves that control pressure and vacuum delivered to the microfluidic valves to open and close during operation.

Pump Assembly: A pump assembly including four 250-µL pumps. The pumps are non-pulsatile flow, self-priming, precision micro-syringe-like pumps. Maximum pump volume per stroke is 250 µL with a maximum flow rate of 8 µL/sec and a minimum flow rate of 5 nano-Liter/sec.

Pump Assembly Electronics: The pump assembly electronics contain the motor controller hardware for controlling the individual stepper motors used to operate the pumps and the manifold's select number of pneumatic valves, and the system power supply.

Performance Requirements

From the time of card insertion and after loading reagents, the isolation and binding step should require no more than minutes. After the thermo cycling (incubation) process, the diagnostic test should require no more than minutes.

The instrument shall be constructed such that all components can be used under ordinary laboratory conditions (10-30° C. and 5%-90% relative humidity) and be operable up to 10,000 feet above sea level. The instrument shall be able to withstand ordinary cleaning agents and exposure to the solutions used during the assay.

The reliability of the instrument shall be such that the system shall run, on average, 100 cartridges before service is required. Once daily, a rinse process is to be performed which clears out air from the pump assembly. A rinse cartridge will be supplied for this preventative maintenance step.

The instrument without PC, shall weigh less than 25 lbs and shall be configured so as to be hand portable.

Compatibility Requirements

The instrument shall be compatible with a PC with the following specifications: minimum Pentium or Celeron 333 MHz minimum microprocessor with minimum 128 MB RAM; minimum 1 Gbyte hard drive; CD ROM for software installation; minimum of 1 serial port; operating system of Windows NT (Service pack 3.0 or later), Windows 98, Windows 2000 or Windows ME.

The instrument shall be compatible to aqueous fluids of pH 1 through 13. Pumps shall be compatible to fluorinert pusher fluid and TRIS wash buffer. The instrument will have a power requirement of 100-240 VAC 50/60 Hz with 2 15A outlets. The instrument shall be compatible with normal laboratory cleaning agents.

Description of Software

SADD/S operating software allows the user control of the instrument and controls the functions of the instrument. The SADD/S operating software is a component of a complete instrument system that includes a motion controller, the personal computer (PC), a cartridge manifold and cartridges.

This software will interface with the existing motion control system, for example an Olsson motion control system, along with an off-the-shelf motion controller in a PC, for controlling pumping of fluids and the vacuum/pressure box for providing vacuum and pressurized air for cartridge valve actuation.

Performance Requirements

The SADD/S operating software will consist of the Graphical User Interface, interfaces either the motion controllers via RS232 cable or off-the-shelf controller via the PC computer back plane, and user safety.

The SADD/S operating software allows the user to control signals from the motion control system that are passed through to motor amplifier boards. The pump status and control signals from the motor amplifier boards are passed to the motion control system where the user is informed of the system status.

The SADD/S operating software may further provide on/off control of vacuum and pressurized air used to control the card valves. The SADD/S operating software provides full user control of all elements. The SADD/S operating software may have a hidden in-house mode available by keystroke that allows for maintenance.

Compatibility Requirements

The SADD/S operating software shall be compatible with a PC with the following specifications: minimum Pentium or Celeron 333 MHz minimum microprocessor with minimum 128 MB RAM; minimum 1 G-byte hard drive; CD ROM for software installation; minimum of 1 serial port; operating system of Windows NT (Service pack 3.0 or later), Windows 98, Windows 2000 or Windows ME.

The SADD/S operating software shall be compatible with standard I/O and motor controllers, for example, Olsson I/O and Motor Controllers. The SADD/S operating software shall be compatible with off-the-shelf PC resident motor controller.

Recommended Miscellaneous Compatibility Requirements.

The O/S shall clearly define an emergency stop button. The O/S menu layout shall conform to the standard layout used in Microsoft products (File on left, Help on right, etc). All controls shall be large enough to be easily manipulated and spaced to avoid unintentional activation.

The status of controls and displays shall be discernable on a black and white screen. Pop-up tips shall be provided. Help files shall be provided. Often used menu items shall be defined as a keystroke. No menu nesting beyond two deep. O/S user screen shall be colored so as to reduce eyestrain. Wherever possible, the user shall be prevented from entering an incorrect value or activating an incorrect control. Wherever possible, a minimum font size shall be 12 point.

Use and Operation

One intended use of the Single Analyte Diagnostic Device/System (SADD/S) is to determine the presence of bacteria such as *E. coli* in water. A filtered water sample will be introduced onto the diagnostic card where device system will isolate and amplify DNA from the water sample. The amplified DNA will then be exposed to a proprietary lateral flow detection strip that will be used for a diagnostic reading.

As illustrated in the flowcharts of FIGS. 4A and 4B, and in table format in FIG. 4C, the operation of the system is as follows:

The user will first capture the sample through a filter module and filtering process. The filter module will be compatible to a disposable diagnostic microfluidic card by either attachment of the module to the card or manufacture of the module in the card. (See FIGS. 7A and 7B)

After acquiring the sample, the user will remove the filter module from the filtering apparatus and insert the filter module into the disposable microfluidic card. Alternatively, the filter module or membrane may be mounted in the microfluidic card.

The user will then insert the card, which contains the sample, into the manifold of the computer control instrument for the purpose of doing a diagnostic evaluation of the target material contained on the membrane.

Prior to running the instrument process, the user should check that the instrument will have a minimum amount of wash buffer. This wash buffer will be consumed during each test sample run.

Prior to running the diagnostic test, the user should check that the instrument has a minimum volume of pushing buffer (typically fluorinert) for pumps 2, 3 and 4.

Prior to initiating the process, the user will pipette (load) the following solutions on the card prior to running the test:

Induction solution—20-40 µl (estimated volume)
Series II Lysing solution—20-40 µl (estimated volume)
NASBA without enzyme solution—4-40 µl (estimated volume)
NASBA Enzyme solution—4-8 µl (estimated volume)
Detection Probe solution—2.5-5.0 µl (estimated volume)

The user will initialize the instrument and initialize the RUN process. The RUN process will start the fluidic steps to control the flow of wash buffer, induction and detection solutions, which will isolate and bind the targeted DNA to the filter membrane material. An exemplary RUN process is outlined in FIG. 3B. The flow rates and pumped volumes are listed in the table. All waste products from the RUN process will be contained on the card.

After completing the RUN process (isolation and binding step), the technician will begin the thermo cycling/incubation process used to amplify the DNA signal. The disposable card will be removed from the instrument manifold and the thermo cycling process will be completed on a commercial thermal cycler.

In an alternative embodiment, the thermal cycler is not part of the instrument, in yet another embodiment, the instrument manifold will be designed to mate with an existing commercial thermal cycler and provide a capability for the card to remain in the manifold while being thermally cycled per requirements.

Figure 8:
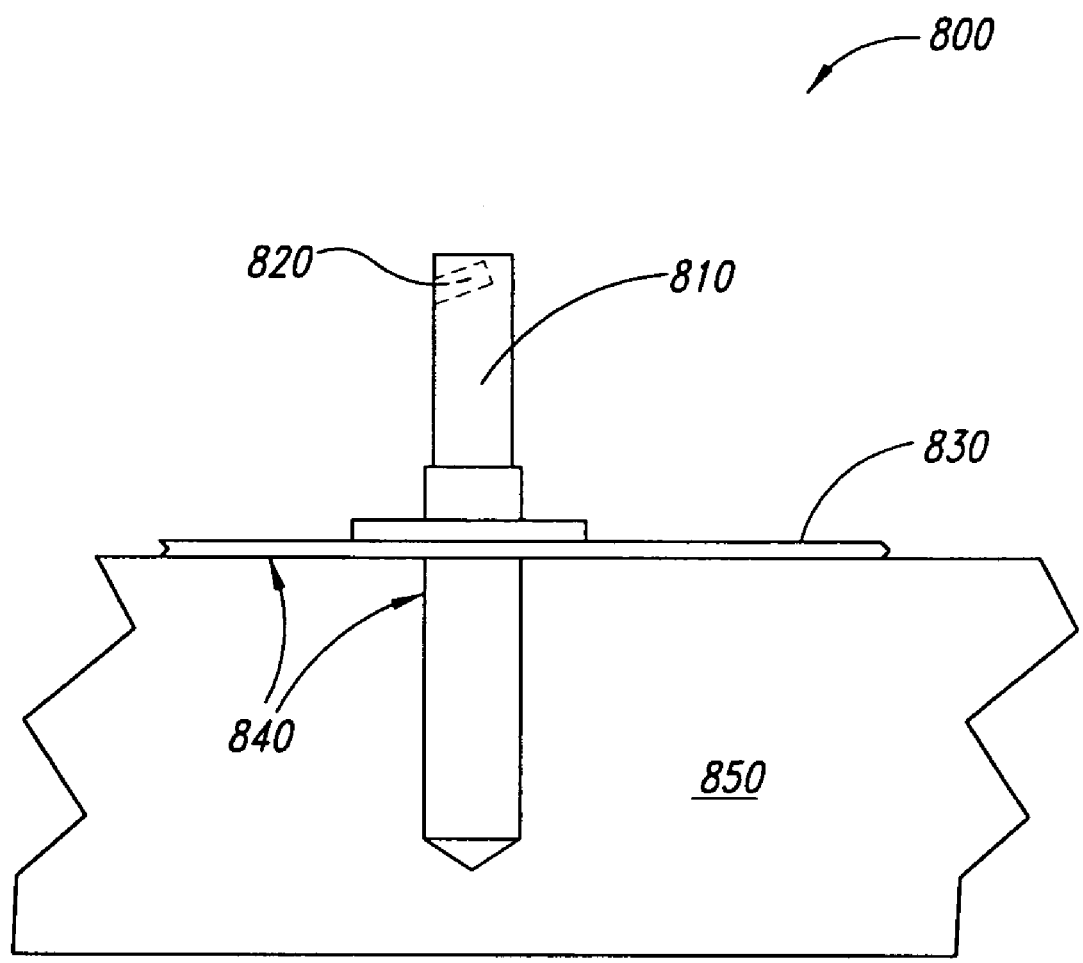
FIG. 8 is a cross-sectional view of a heat transfer rod and plate mounted in the heater block in accordance with principles of the present invention.
Figure 9:
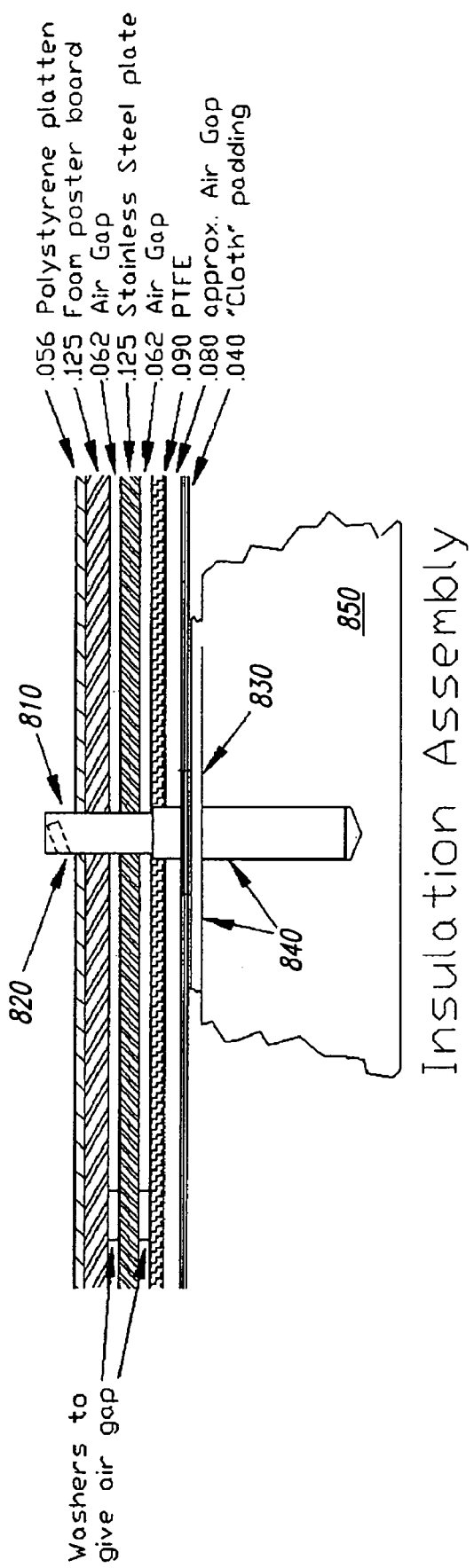
FIG. 9 is a cross-section of an insulation and platen assembly in accordance with principles of the present invention.

FIG. 8 illustrates one embodiment of a thermo cycler for use with the present invention. FIG. 8 is a cross-sectional view of a heat transfer rod and plate mounted in a heater block in accordance with principles of the present invention. The heat transfer system of FIG. 8 includes a rod 810, a temperature control sensor hole 820 in the rod 810, a Thermal-Lok dry bath heater block 850. The rod 810 extends into the heater block 850. A plate 830 encircles the rod 810, and a silicone thermal compound 840 fills any voids between the rod 810 and the heater block 850. A temperature control sensor probe (not shown) is inserted in the temperature control sensor hole 820, the thermocouple is connected to the plate 830, and the surface temperature of the top of the platen is monitored. The rod 810 and the plate 830 may be made of brass or any other heat conducting metal. FIG. 9 is a cross-section of an insulation and platen assembly in accordance with principles of the present invention.

Figure 10:
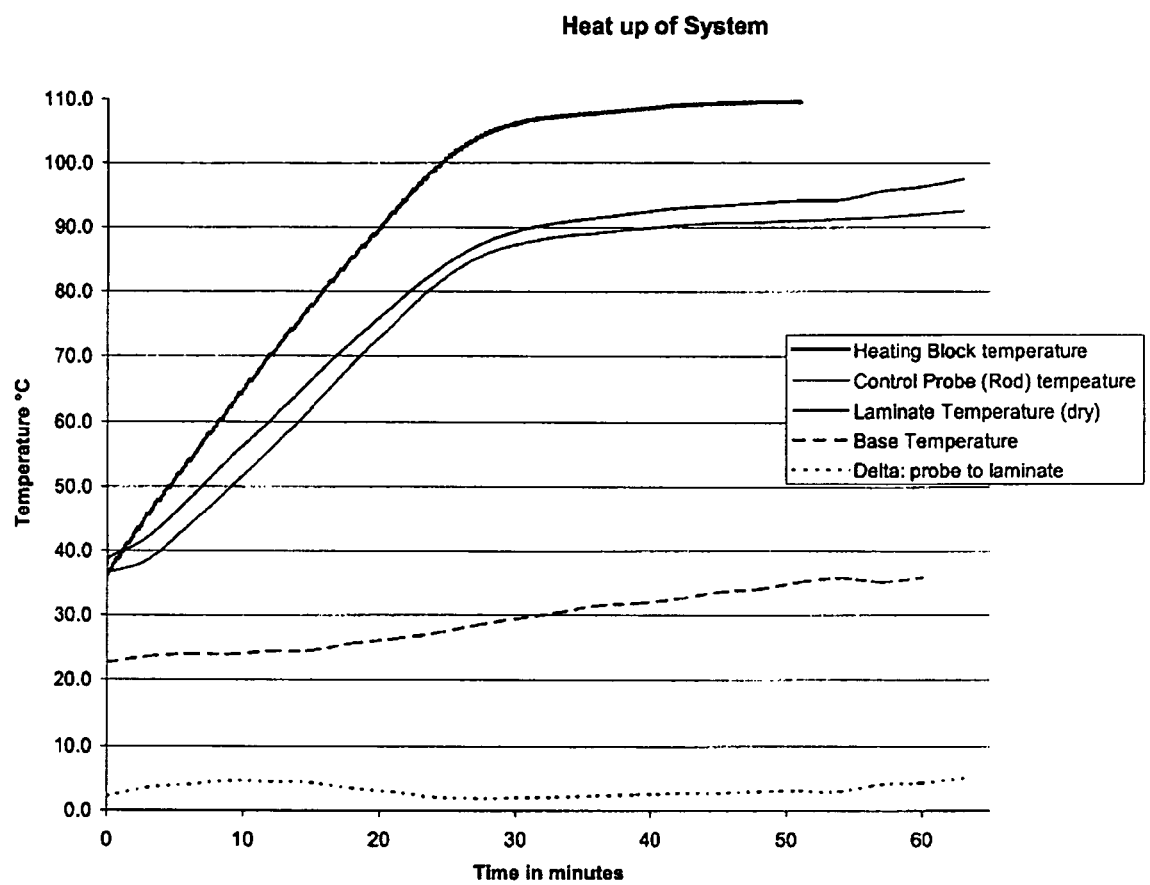
FIG. 10 is a chart of temperature vs. time to heat the system in accordance with principles of the present invention.
Figure 11:
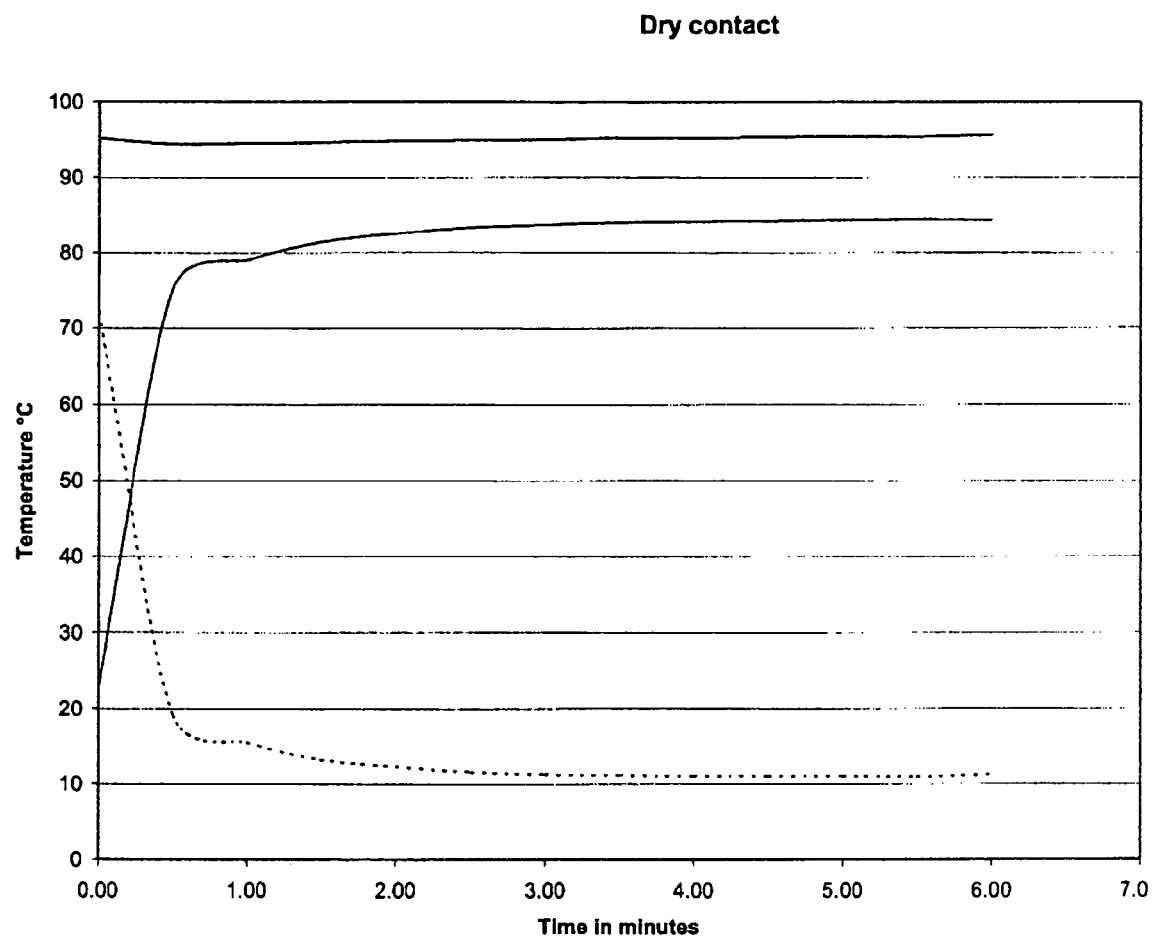
FIG. 11 is a graph of temperature vs. time in accordance with principles of the present invention.
Figure 12:
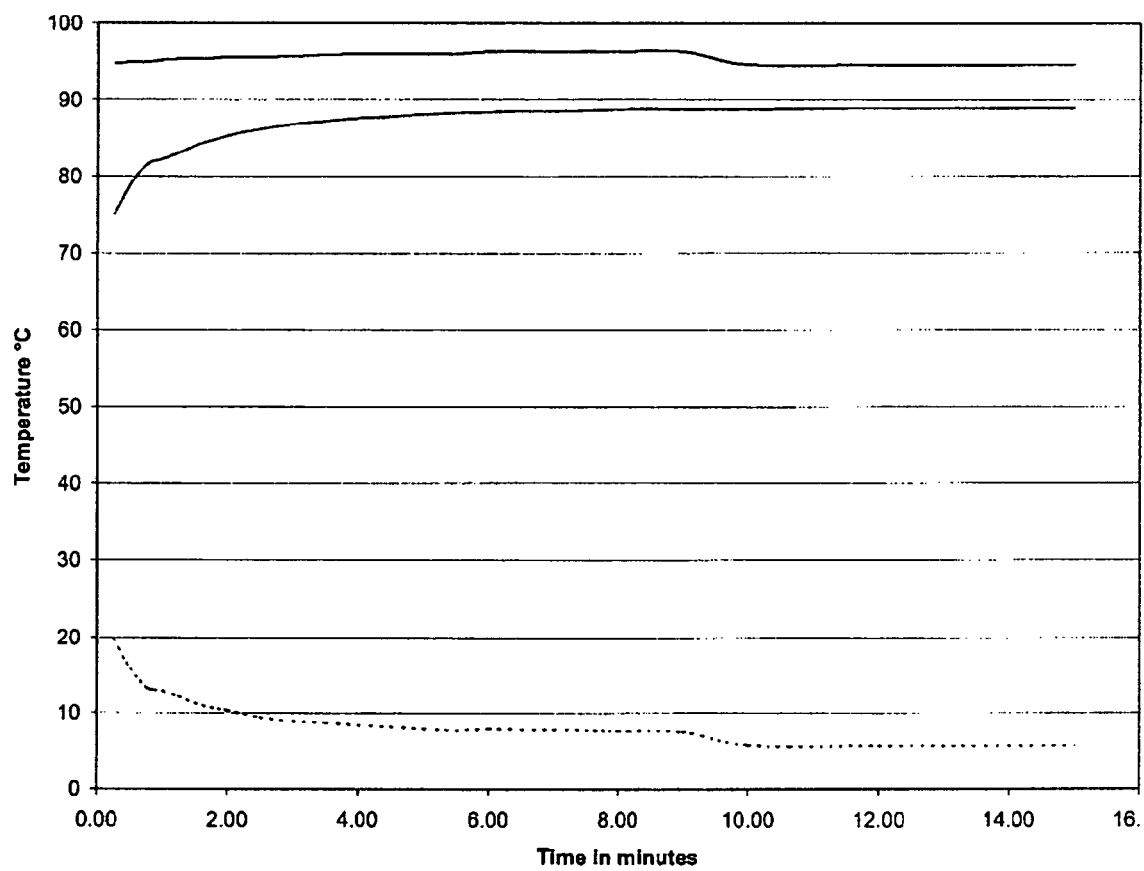
FIG. 12 is a graph of temperature vs. time in accordance with principles of the present invention.
Figure 13:
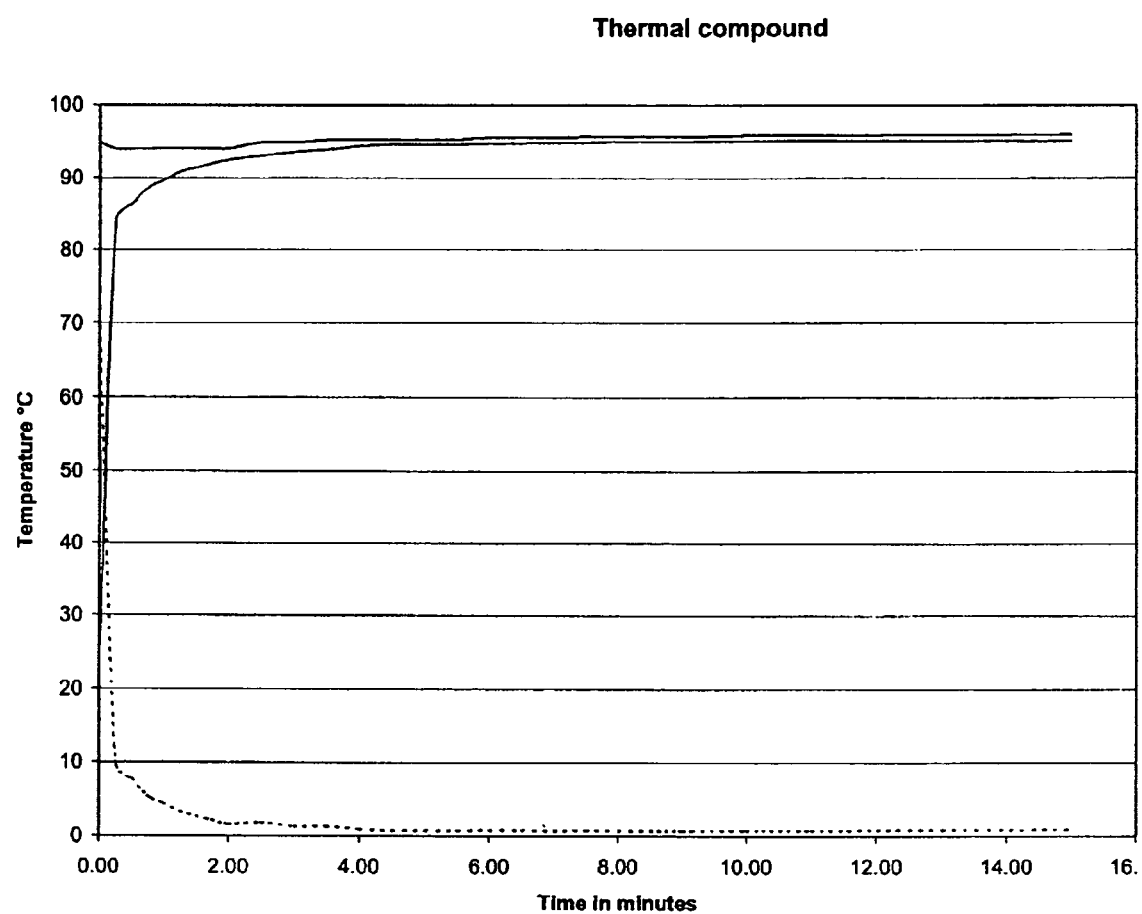
FIG. 13 is a graph of temperature vs. time in accordance with principles of the present invention.
Figure 14:
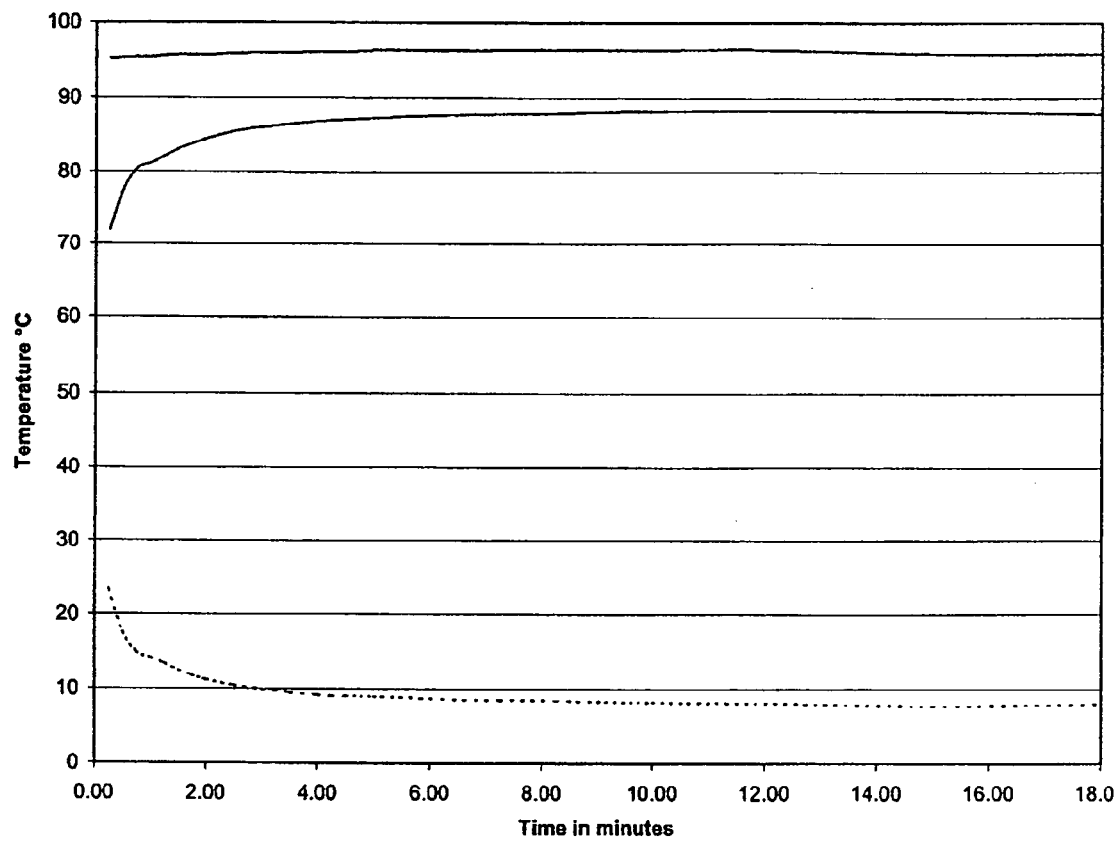
FIG. 14 is a graph temperature vs. time in accordance with principles of the present invention.

FIGS. 10-14 are graphs illustrating principles of the present invention in accordance with the above described thermo cycler. FIG. 10 is a chart of temperature vs. time to heat the system in accordance with principles of the present invention. FIG. 11 is a graph of temperature vs. time in accordance with principles of the present invention. FIG. 12 is a graph of temperature vs. time in accordance with principles of the present invention. FIG. 13 is a graph of temperature vs. time in accordance with principles of the present invention. FIG. 14 is a graph temperature vs. time in accordance with principles of the present invention.

The thermo cycling process is identified to be as follows:

| Thermo-Cycling Process | | |
| --- | --- | --- |
| Time (min) | Temperature (° C.) | Temperature Tolerance (° C.) |
| 30-120 | 37 | 0.5 |
| 2 | 65 | 0.5 |
| 90 | 40 | 0.5 |
| 1 | 95 | 0.5 |

Following the thermo cycling process, the user will reinstall the card onto the instrument for the Detection Process step. This will open a channel to the lateral flow detection strip and pump wash buffer across the membrane. This will expose the detection strip to the chemical product for detection.

After allowing for the appropriate exposure time, the user will read the lateral flow detection strip to determine the presence or absence of the target.

After reading the detection strip, the card will be removed from the instrument and discarded. All waste products from the sample will be contained on the card.

Yet another use of the Single Analyte Diagnostic Device/System (SADD/S) is to determine the presence of sexually transmitted diseases from urine. A urine sample will be introduced onto the diagnostic card where the device system will isolate and amplify the DNA from urine for the detection of sexually transmitted diseases.

The following examples are provided for illustrative purposes and are not intended to limit the invention in any way.

EXAMPLE 1

Card/Manifold Testing Thermal Transfer to Micronics Laminate from Thermal-Loc Dry-Bath Goal:
Determine efficiency and method of transferring heat from the Thermal-Lok Dry-Bath heat plate to a localized interface to a microfluidic laminate.
The Laminate to be held by a Micro Hydro Manifold (MHM).
Heat transfer to small-localized area of laminate. Temperature to be 60° C. to 95° C. The rest of the card to be isolated from the heat as much as possible.
Temperature Control to be as close to laminate as possible.
Micro Hydro Manifold (MHM) and its mounting platform are to be insulated from the heat source.

SUMMARY

The ability to transfer heat in a controlled way through a 4 mil laminate layer is clearly achievable. The best results were achieved by using a thin layer of the "wet" silicone thermal grease to couple the polyester surface to the brass. Further testing should be done to establish the temperature of a wet fluid filled chamber of the size that will be used. Our past experience has indicated that this should follow the bottom polyester temperature very closely as the liquid will conduct heat much better than mylar and the thermal diffusion over such a small volume will allow for nearly uniform temperature. Testing can confirm this.

Recommendations:
The Thermal-Lok Dry-Bath can be used the temperature source for DNA amplification and de-stranding of DNA.

Equipment:
Thermal-Lok Dry-Bath with external temperature control probe.
USA Scientific Inc.
Fluke 52 Thermometer
0.005 dia. Type K thermocouple mounted on Micronics µfluidic card. Covered by 0.004 Mylar.
Thermolink 1000 Silicone Thermal Joint Compound. P/N 000006 MVID Thermal Technology Inc. Laconia N.H.
Brass Heat Rod and insulation plate. Interface Diameter 0.250".
Micro Hydro Manifold
Insulated Platen Tests Performed:
Total time to heat up the system.
Temperature of heater.
Temperature of Heat Transfer Rod at laminate end.
Temperature of laminate.
Temperature of Platen.
Maximum temperature of platen.
Time to heat laminate with system preheated to operating temperature. Laminate is placed on heater to start test.
Dry contact interface.
"Wet" silicone compound interface.
Silicone elastomer on rod.
Silicone elastomer on laminate.

Setup:
A brass heat transfer rod was manufactured to fit into one of the holes in the Thermal-Lok Dry-Bath heat plate. After it was determined that the heat transfer needed to be more efficient a flat brass plate covering the whole heater was soldered to the heat transfer rod.
The rod has a top diameter of 0.250" and a small hole in its side for the temperature control probe. The rod is also long enough to give room for insulation plates to shield the rest of the manifold and card.
The platen insulation material is polystyrene. The platen top plate to hold the MHM (Micro hydro Manifold) is fabricated using the insulating material.
See figures for details of the heat transfer rod and insulation.

Data Continued:

The Delta Temperature, the temperature difference between the Heat Transfer Rod at the sensor probe and the Laminate, shows that we loose a significant amount of heat at the interface. Samples were recorded every 30 seconds in an open room. Some improvement may be gained by covering the card and blocking the airflow paths to the brass-heating rod to prevent ambient room temperature fluctuations and air currents from affecting the results.

| Coupling Method | Delta Temperature (° C.) | Rod Std. Dev. (° C.) | Mylar Std. Dev (° C.) | Delta Std. Dev. (° C.) |
|---|---|---|---|---|
| Dry | 11.0° C. | .148 | .114 | .109 |
| Silicone compound "wet" | 0.8° C. | .238 | .224 | .074 |
| Silicone elastomer on rod | 5.7° C. | .706 | .412 | .958 |
| Silicone elastomer on laminate | 8.0° C. | .198 | .702 | .634 |

The "wet" Thermolink 1000 compound is the most efficient as seen by the smallest temperature delta. It is a bit messy from the standpoint of having to apply it prior to putting the cartridge on, but for preliminary feasibility testing it should be OK.

The elastomer is an improvement over a dry contact. There are several types readily available that are used as heat sink pads for electronics. The pads could be mounted on or in the laminate or on the rod end. Further tests could be performed with the different materials to determine the best for this application.

The delta in temperature is an important measurement because it eliminates the possibility of coupling variation between heater and laminate changing thus allowing temperature variation. However, the other important parameter is temperature stability. The standard deviation of the samples and the delta temperature beginning at 4 minutes after coupling the heater and card were calculated and are shown in the table above. In three of the 4 cases the polyester temperature was actually more stable than the rod temperature. Factoring out the variations in the controlled rod by looking at the Delta standard deviation, it becomes clear that in all of the cases the variation of mylar temperature was less than a degree different from the rod temperature. If the rod temperature is well controlled, the polyester temperature will be stable as well.

Any of the coupling methods appear stable enough, but clearly the "wet" silicone compound coupling is the most controlled and closest to the set temperature in the brass tip.

Notes:

The size of the Heat Transfer Rod end was based on a rough guess on the size of the laminate fluid chamber. A smaller or larger interface area will affect the heat transfer rate accordingly.

The data from the silicone pad on rod shows a decrease in temperature that does not show up in the polyester temperature. It is assumed here that the thermocouple's contact in the heater rod may have shifted making a less efficient thermal connection.

It should also be noted that the thermocouple imbedded in the laminate had solid Mylar behind it. It was not measuring the temperature in a "chamber" but the temperature of the laminate 0.004" above the surface of the heater.

Process:
  For all pumps:
    1) Fill sample reservoirs with pipette. (V3, V4 valves closed & V5 valves open)
    2) Fill "A" amplification chamber. (V4, V5 valves closed & V3 valves open)
    3) Fill "B" amplification chamber. (V3, V5 valves closed & V4 valves open)
    4) Place card on specially designed heater block.
    5) Oscillate pumps back and forth at slow rate (~10 uL moved) alternating between A & B amplification chambers
    6) After 90 minutes heating move amplification mixture to output for pipette removal.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for microfluidic analysis of a fluid sample, comprising:
  loading a microfluidic card with a fluid sample;
  lysing the fluid sample to separate components of the fluid sample;
  capturing the separated components on a solid substrate;
  washing the separated components with wash buffers;
  amplifying the washed components in an the amplification chamber; and
  pumping the amplified components over a lateral flow strip for detection.

2. The method of claim 1 wherein the separated components are bacteria.

3. The method of claim 1 wherein the washing includes removing nucleic acid to prohibit interference with the amplifying the washed components.

4. The method of claim 2 wherein the bacteria are *Escherichia. coli.*, *Staphylococcus aureus*, *Pseudomonas aeruginosa*, *Salmonella* spp., *Staphylococcus epidermidis*, *Klebsiella pneumoniae*, *Enterobacter cloacae*, β-*Streptococcus*, *Serratia marcescens*, and/or *Bacillus cereus*.

5. The method of claim 1 further including priming the separated components with DNA primers.

6. The method of claim 1 wherein the pumping includes visually detecting the presence of bacterial DNA on the lateral flow strip.

7. The method of claim 1 further including engaging the microfluidic card with a manifold of an instrument for purposes of pumping the fluid sample through the card.

8. A method of microfluidic analysis of a fluid sample on a microfluidic card, comprising:
  collecting a fluid sample;
  filtering the fluid sample through a membrane module wherein target cellular material is retained on membrane;
  passing a wash buffer across the membrane such that target cellular material remains on the membrane;
  passing induction solution across membrane;
  passing a lysing solution across the membrane;
  passing a wash buffer across the membrane to wash the lysing solution from the membrane;
  passing a first NASBA solution across the membrane;

passing a wash buffer across the membrane to wash the first NASBA solution from the membrane;
passing a second NASBA solution across the membrane;
passing a wash buffer across the membrane to wash the second NASBA solution from the membrane;
passing a detection solution across the membrane;
amplifying a RNA signal by thermo-cycling the cellular material;
washing the detection probe solution from the membrane; and
exposing the washed detection probe solution to a lateral flow strip for visual detection of RNA.

9. The method of claim 8 wherein the membrane module is removed from a filtration apparatus and inserted into the microfluidic card.

10. The method of claim 8 wherein the induction solution is pipetted onto the card.

11. The method of claim 8 wherein the second NASBA solution includes enzymes.

12. The method of claim 8 wherein the microfluidic card in fluidly engaged with the manifold of a fluidic instrument for pumping the fluid throughout the card.

13. The method of claim 9 wherein the microfluidic card is removed from the fluid engagement of the manifold and detachably connected to a thermo-coupler for the amplification of the RNA signal.

* * * * *